United States Patent [19]

Hobbs et al.

[11] Patent Number: 5,200,419
[45] Date of Patent: Apr. 6, 1993

[54] SUBSTITUTED TETRAZOLES AND DERIVATIVES THEREOF ACTING AT MUSCARINIC RECEPTORS

[75] Inventors: Sheila H. Hobbs, Dexter; Haile Tecle, Ypsilanti, both of Mich.

[73] Assignee: Warner-Lambert Company, Morris Plains, N.J.

[21] Appl. No.: 526,423

[22] Filed: May 21, 1990

[51] Int. Cl.$^5$ .................. C07D 211/36; C07D 401/06
[52] U.S. Cl. ................................ 514/323; 546/187; 546/188
[58] Field of Search ................ 548/250; 546/187, 188; 514/323

[56] References Cited

U.S. PATENT DOCUMENTS

| | | | |
|---|---|---|---|
| 2,470,084 | 5/1949 | Harvill et al. | 548/250 |
| 3,767,667 | 10/1973 | Kamiya et al. | 548/250 |
| 4,372,953 | 2/1983 | Uchida et al. | 546/276 |
| 4,563,455 | 1/1986 | Ueda et al. | 514/241 |
| 4,791,210 | 12/1988 | Bison et al. | 548/250 |
| 4,900,839 | 2/1990 | Campbell et al. | 548/250 |

FOREIGN PATENT DOCUMENTS 0296721 12/1988 European Pat. Off. .

OTHER PUBLICATIONS

Chemische Berichte, 103, pp. 2821–2827 (1970) Reimlinzer, H., et al.
Liebigs Annalen der Chemie, 725, pp. 29–36 (1969) Zbiral, E., & Stroh, J.

Primary Examiner—C. Warren Ivy
Assistant Examiner—Raymond Covington
Attorney, Agent, or Firm—Francis J. Tinney

[57] ABSTRACT

Substituted tetrazoles and derivatives thereof are described, as well as methods for the preparation and pharmaceutical compositions of same, which are useful as centrally acting muscarinic agents and are useful as analgesic agents for the treatment of pain, as sleep aids and as agents for treating the symptoms of senile dementia, Alzheimer's disease, Huntington's chorea, tardive dyskinesia, hyperkinesia, mania, or similar conditions of cerebral insufficiency characterized by decreased cerebral acetylcholine production or release.

3 Claims, No Drawings

SUBSTITUTED TETRAZOLES AND DERIVATIVES THEREOF ACTING AT MUSCARINIC RECEPTORS

BACKGROUND OF THE INVENTION

The present invention relates to novel substituted tetrazoles and derivatives thereof useful as pharmaceutical agents, to methods for their production, to pharmaceutical compositions which include these compounds and a pharmaceutically acceptable carrier, and to pharmaceutical methods of treatment. More particularly, the novel compounds of the present invention act at muscarinic receptors and may be useful in treating the symptoms of cognitive decline in an elderly patient.

Disorders of cognition are generally characterized by symptoms of forgetfulness, confusion, memory loss, attentional deficits and/or, in some cases, affective disturbances. These symptoms may arise as a result of the general aging process and/or from organic brain disease, cerebrovascular disease, head injury or developmental or genetic defects.

The general decrease in cognitive function which accompanies the aging process is well accepted. The same phenomenon has been observed and documented in many lower mammals, including those routinely employed in pharmacological testing programs for screening and predicting usefulness for particular drugs in higher animals, including humans.

Although disorders of cognition often accompany the general aging process, presenile and senile primary degenerative dementia are the most common accepted causes of mental deterioration in the elderly. It has been estimated that at least ten percent of persons over sixty years of age will eventually suffer severe mental deterioration. A much larger number will experience cognitive decline of sufficient severity to impede their activities.

Many of the symptoms of cognitive disorders, especially impaired memory, are associated with decreased acetylcholine synthesis and the impairment of cholinoreceptive neurons. In the hippocampus and cerebral cortex of patients suffering from primary degenerative dementia for example, the level of the enzyme choline acetyltransferase (CAT) can be reduced as much as ninety percent (see Davies, P., et al, The Lancet, 2, page 1403 (1976); Perry, E. K., et al, Journal of Neurological Sciences, 34, pages 247-265 (1977); and White, P., et al, The Lancet, 1, pages 668-670 (1977)).

Since CAT catalyzes the synthesis of acetylcholine from its precursors choline and acetyl coenzyme A, the loss of CAT reflects the loss of cholinergic or acetylcholine-releasing nerve endings in the hippocampus and cerebral cortex. There is abundant evidence that cholinergic terminals in the hippocampus are critically important for memory formation.

The cholinergic hypothesis suggests that drugs which restore acetylcholine levels or cholinergic function (i.e., cholinomimetic) are effective in correcting this deficit in neurotransmitter chemical and provide treatment of the memory impairment symptom of cerebral insufficiency. Considerable biochemical, pharmacological, and electrophysiological evidence supports the hypothesis that deficits in the cholinergic system underlie geriatric cognitive dysfunction (Peterson, C. and Gibson, G. E., Neurobiology of Aging, 4, pages 25-30 (1983)). Aged humans and nonhuman primates with decreased cognition show improved memory when they are treated, for example, with acetylcholinesterase inhibitors such as physostigmine. These agents increase the available supply of synaptic acetylcholine by inhibiting its hydrolysis.

Aminopyridines such as 3,4-diaminopyridine ameliorate age-related cognitive deficits by increasing the release of acetylcholine from presynaptic nerve terminals, thus increasing synaptic acetylcholine (see Davis, H. P., et al, Experimental Aging Research, 9, pages 211-214 (1983)).

It has been known for some time that the natural alkaloid, muscarine, has the ability to act relatively selectively at autonomic effector cells to produce qualitatively the same effect as acetylcholine. Two other agents, pilocarpine and oxotremorine, have the same principal sites of action as muscarine and acetylcholine and are thus classified as having "muscarinic" action.

It is well known that the cholinergic hypothesis suggests that cholinomimetics, including muscarinic agents, may have potential in treating senile cognitive decline (SCD). However, the multiple development issues associated with cholinomimetics, including, for example, poor bioavailability, short duration of action, and especially parasympathetic side effects, have diminished hopes of adequate therapy with this class of agents.

A series of fused imidazole compounds represented by the formula

wherein
A is lower alkylene,
$R^1$ is hydrogen, lower alkyl, lower alkoxy or halogen,
$R^2$ is hydrogen, lower alkyl, cyclo(lower)alkyl, pyridyl, ar(lower)alkyl which may be substituted with halogen, or aryl which may be substituted with lower alkyl, lower alkoxy, hydroxy or halogen,
$R^3$ is N-containing unsaturated heterocyclic group which may be substituted with lower alkyl or amino, and
Y is =C— or =N— useful as antiulcer agents is disclosed in U.S. Pat. No. 4,563,455.

A series of heterocyclic compounds represented by the formula where the dotted line designates an optional bond

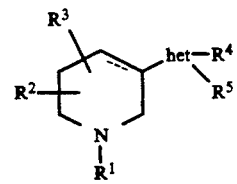

wherein "het" designates a five-membered heterocyclic ring which may include one or two double bonds and one to four heteroatoms selected from nitrogen, oxygen or sulphur, provided that "het" may not designate a 1,2,4- or 1,3,4-oxadiazole;

$R^1$ is selected from hydrogen, lower alkyl optionally substituted with phenyl which may be substituted with halogen, lower alkyl, or lower alkoxy, or a group $R^6$—CO—NH—CH$_2$— or $R^6$—O—CO— where $R^6$ is lower alkyl, branched or unbranched, or phenyl optionally substituted with halogen, trifluoromethyl, lower alkyl, hydroxy, lower alkoxy, or lower acyloxy;

$R^2$ and $R^3$ are the same or different, each representing hydrogen, lower alkyl, cycloalkyl (three to six carbon atoms), lower alkenyl, lower alkadienyl, lower alkynyl, optionally substituted with hydroxy, halogen, or phenyl in which the phenyl group may be substituted with halogen, trifluoromethyl, lower alkyl, hydroxy or lower alkoxy; $R^2$ and $R^3$ may further, respectively, be selected from trifluoromethyl or phenyl optionally substituted with halogen, trifluoromethyl, lower alkyl, hydroxy, lower alkoxy, or lower acyloxy, or $R^2$ and $R^3$ may, respectively, be a group $OR^7$ or $SR^7$ where $R^7$ is defined as $R^2$ or $R^3$, and if "het" includes two or more carbon atoms, $R^4$ and $R^5$ are the same or different, and each is defined as $R^2$ or $R^3$ and if "het" includes only one carbon atom, there is only one substituent, $R^4$, on the heterocyclic ring, and $R^4$ is defined as $R^2$ or $R^3$, as well as individual stereoisomers and pharmaceutically acceptable acid addition salts thereof useful for the treatment of disorders caused by malfunction of the acetylcholine or muscarinic system is disclosed in European Patent Application 0296721.

A series of substituted tetrazoles of the formula

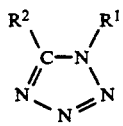

wherein $R^1$ is β-naphthyl, α-naphthyl, α-pyridyl or phenylethyl and $R^2$ is CH$_3$—, CF$_3$—, (CH$_3$)$_2$CH—, trans—CH$_3$—CH=CH— or trans,trans—CH$_3$—CH=CH—CH=CH— is disclosed by Zbiral, E. and Stroh, J., *Liebigs Annalen der Chemie,* 725, pages 29-36 (1969).

3(5)-Tetrazolyl-(1)]-pyrazole is disclosed by Reimlinzer, H., et al, *Chemische Berichte,* 103, pages 2821-2827 (1970).

However, none of the compounds disclosed in the aforementioned references suggest the combination of structural variations of the compounds of the present invention described hereinafter. Furthermore, the aforementioned compounds are not disclosed for treating the symptoms of cognitive decline in an elderly patient.

The substituted tetrazoles and derivatives thereof of the present invention may have affinity for the muscarinic receptor and thus are expected to be useful in the treatment of the symptoms of cognitive decline in an elderly patient including Alzheimer's disease.

SUMMARY OF THE INVENTION

Accordingly, the present invention is a compound of Formula I

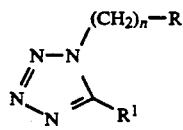

I wherein R is selected from the group consisting of

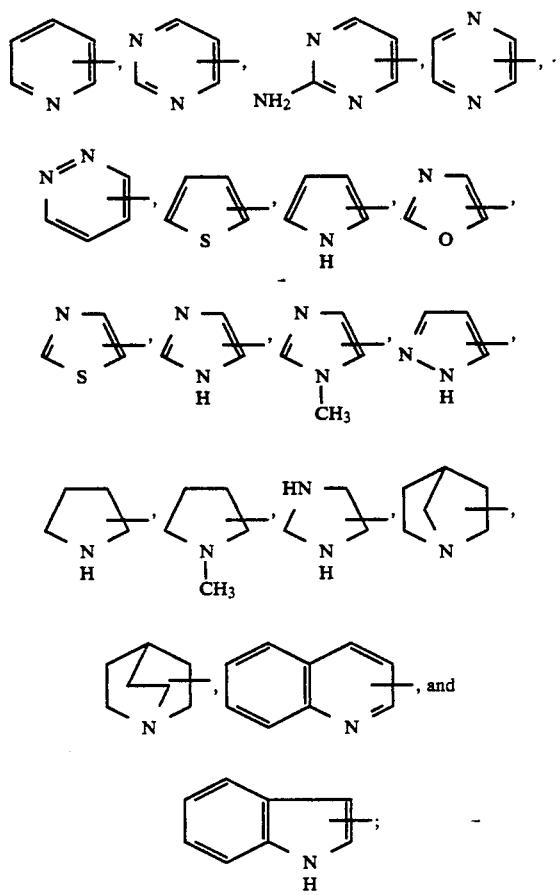

$R^1$ is hydrogen, alkyl of from one to ten carbon atoms, alkynyl of from two to ten carbon atoms or aryl; n is zero or an integer of one or two; or a pharmaceutically acceptable acid addition salt thereof with the exclusion of compounds of formulas

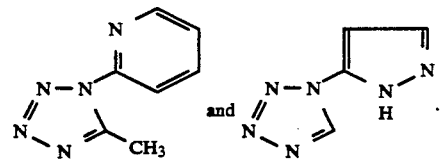

and

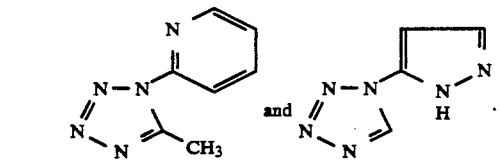

As centrally acting muscarinic agents, the compounds of Formula I are useful as analgesic agents for the treatment of pain in mammals including man, as sleep aids, and as agents for treating the symptoms of senile dementia, Alzheimer's disease, Huntington's chorea, tardive dyskinesia, hyperkinesia, mania or similar conditions of cerebral insufficiency characterized by decreased cerebral acetylcholine production or release.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "alkyl" means a straight or branched hydrocarbon radical having from one to ten carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, and the like.

The term "alkynyl" means a straight or branched triple bonded unsaturated hydrocarbon radical having from two to ten carbon atoms and includes, for example, ethynyl, 2-propynyl, 1-butynyl, 2-butynyl, 3-butynyl, 1-pentynyl, 3-pentynyl, 1-hexynyl, 2-hexynyl, 3-hexynyl, 3-heptynyl, 1-octynyl, 2-octynyl, 1-nonynyl, 2-nonynyl, 3-nonynyl, 4-nonynyl, 1-decynyl, 2-decynyl, and the like.

The term "alkoxy" means alkyl-O- of from one to ten carbon atoms as defined above for "alkyl".

The term "thioalkoxy" means alkyl-S- of from one to ten carbon atoms as defined above for "alkyl".

The term "aryl" means an aromatic radical which is a phenyl group or phenyl group substituted by one to four substituents selected from alkyl, alkoxy, thioalkoxy, halogen or trifluoromethyl such as, for example, benzyl, phenethyl, and the like.

"Halogen" is fluorine, chlorine, bromine, or iodine.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, and galacturonate (see, for example, Berge, S. M., et al, "Pharmaceutical Salts," *Journal of Pharmaceutical Science*, Vol. 66, pages 1-19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free bases for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess asymmetric carbon atoms (optical centers); the racemates as well as the individual enantiomers are intended to be encompassed within the scope of the present invention.

A preferred compound of Formula I is one wherein R is selected from the group consisting of

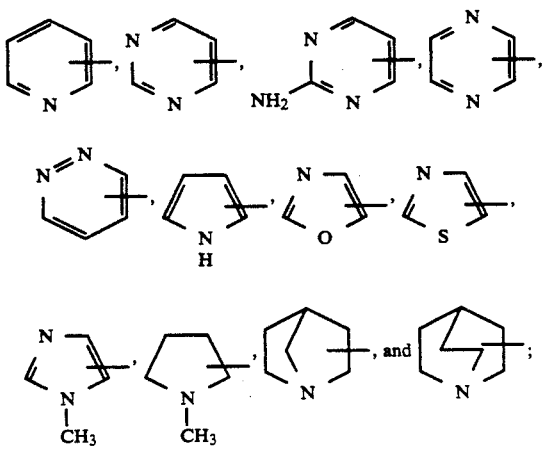

A more preferred compound of Formula I is one wherein R is selected from the group consisting of

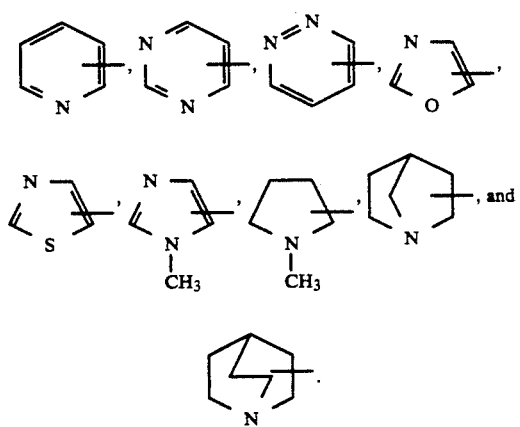

Particularly valuable are:
3-(1H-Tetrazol-1-yl)pyridine;
2-(1H-Tetrazol-1-ylmethyl)pyridine;
4-(1H-Tetrazol-1-ylmethyl)pyridine;
5-(1H-Tetrazol-1-ylmethyl)pyrimidine;
4-(1H-Tetrazol-1-ylmethyl)pyrimidine;
3-(1H-Tetrazol-1-ylmethyl)pyridazine;
4-(1H-Tetrazol-1-ylmethyl)pyridazine;
1-(4-Oxazolylmethyl)-1H-tetrazole;
1-(5-Oxazolylmethyl)-1H-tetrazole;
1-(5-Thiazolylmethyl)-1H-tetrazole;
1-(4-Thiazolylmethyl)-1H-tetrazole;
1-[(1-Methyl-1H-imidazol-5-yl)methyl]-1H-tetrazole;
1-[(1-Methyl-1H-imidazol-4-yl)methyl]-1H-tetrazole;
5-Ethyl-1-[(1-methyl-1H-imidazol-5-yl)methyl]-1H-tetrazole;
3-(1H-Tetrazol-1-ylmethyl)-1-azabicyclo[2.2.1]-heptane;
3-(1H-Tetrazol-1-ylmethyl)-1-azabicyclo[2.2.2]-octane;
3-(1H-Tetrazol-1-yl)-1-azabicyclo[2.2.2]octane;

3-(5-Methyl-1H-tetrazol-1-yl)-1-azabicyclo[2.2.2]octane; and 3-(5-Ethyl-1H-tetrazol-1-yl)-1-azabicyclo[2.2.2]-octane; or a pharmaceutically acceptable acid addition salt thereof.

The compounds of Formula I are valuable centrally acting muscarinic agents. The biological activity of compounds of the present invention was evaluated using a number of tests. The activity of compounds of the present invention as central muscarinic binding site agonists and antagonists is measured. Thus, in the Receptor [$^3$H]Quinuclidinyl Benzilate Binding Assay (RQNB), described more fully by Watson, M., et al, *Journal of Pharmacology an Experimental Therapeutics*, 237, pages 411 to 418 (1986), rat cerebral cortex tissue is treated with radiolabeled quinuclidinyl benzilate, a known muscarinic binding site antagonist. The concentration of test compound required to inhibit 50% of the binding of this muscarinic antagonist is then determined. This procedure allows a determination of the affinity of the test compounds for the central muscarinic antagonist site. Similarly in the Receptor [$^3$H]Cis-methyldioxalane Assay (RCMD), described more fully by Vickroy, T. W., et al, *Journal of Pharmacology and Experimental Therapeutics*, 229, pages 747 to 755 (1984), rat cerebral cortex tissue is treated with radiolabeled cis-methyldioxalane, a known muscarinic binding site agonist. The concentration of test compound required to inhibit 50% of the binding of this muscarinic agonist is then determined. This procedure allows a determination of the affinity of the test compound for the central muscarinic agonist site. The values for the RQNB and RCMD assay are shown in Table I as percent inhibition at 1 μM and 0.1 μM, respectively.

TABLE I

| | Biological Activity of Compounds of Formula I | | |
|---|---|---|---|
| Example Number | Compound | RCMD (% Inhibition at 0.1 μM) | RQNB (% Inhibition at 1 μM) |
| 1 | 3-(1H-Tetrazol-1-yl)-1-azabicyclo-[2.2.2]octane | 0 | 7 |
| 1a | 3-(5-Methyl-1H-tetrazol-1-yl)-1-azabicyclo-[2.2.2]octane | 8 | 19 |
| 1b | 3-(5-Ethyl-1H-tetrazol-1-yl)-1-azabicyclo-[2.2.2]octane | 15 | 11 |

A compound of Formula I

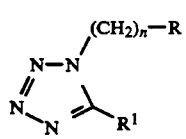

wherein R is selected from the group consisting of

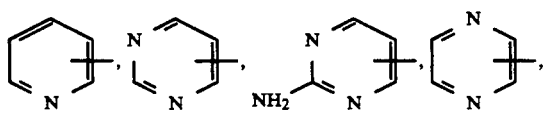

-continued

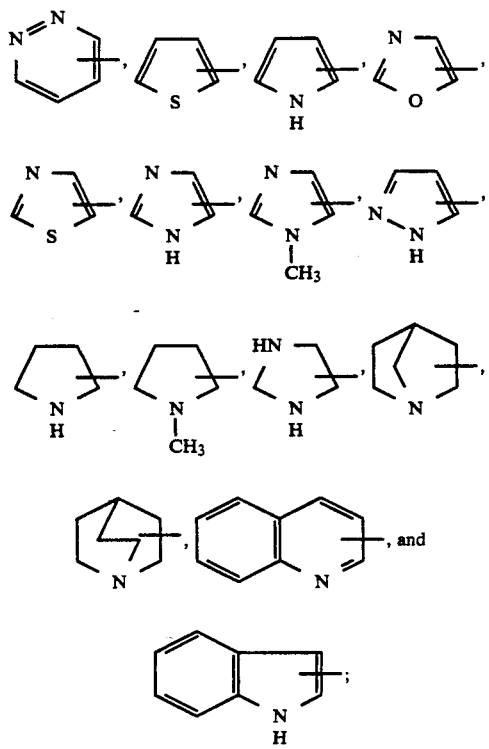

$R^1$ is hydrogen or alkyl of from one to ten carbon atoms, alkynyl of from two to ten carbon atoms or aryl; n is zero or an integer of one or two; or a pharmaceutically acceptable acid addition salt thereof with the exclusion of compounds of formulas

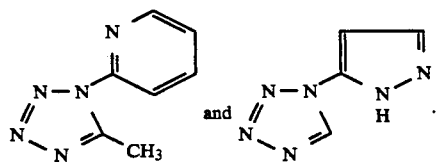

may be prepared by reacting a compound of Formula II $$R-(CH_2)_n-NH_2 \qquad \text{II}$$

wherein R and n are as defined above with a compound of Formula III $$R^1-C(OR^2)_3 \qquad \text{III}$$

wherein $R^2$ is alkyl of from one to six carbon atoms and $R^1$ is defined above in the presence of sodium azide and an acid such as, for example acetic acid and the like to give a compound of Formula I.

Compounds of Formula II and Formula III are either known or capable of being prepared by methods known in the art.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.7 to 7000 mg depending upon the particular application and the potency of the active component. The composition can, if desired, also contain other compatible therapeutic agents.

In therapeutic use as centrally active muscarinic agents the compounds utilized in the pharmaceutical method of this invention are administered at the initial dosage of about 0.01 to about 100 mg per kilogram daily. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

3(1H-Tetrazol-1-yl)-1-azabicyclo[2.2.2]octane

A suspension of 3-aminoquinuclidine dihydrochloride (19.94 g, 0.1 mol), sodium azide (7.8 g, 0.12 mol) and triethylorthoformate (22 mL, 0.15 mol) in glacial acetic acid (50 mL) is heated at an oil bath temperature of 100° C. for 3 hours. The solvent is removed and the oily residue is partitioned between aqueous concentrated potassium carbonate solution and chloroform. The organic layer is dried (potassium carbonate) and concentrated to an oil. The oil is purified by column chromatography (silica gel eluting with chloroform-methanol 8:2) to give 10.82 g of the title compound; mp 83°–84° C. as a white solid.

In a process analogous to Example 1 using appropriate starting materials the corresponding compounds of Formula I are prepared:

EXAMPLE 1a 3-(5-Methyl-1H-tetrazol-1-yl)-1-azabicyclo[2.2.2]-octane; mp 133°–134° C.

EXAMPLE 1b 3-(5-Ethyl-1H-tetrazol-1-yl)-1-azabicyclo[2.2.2]-octane; mp 100°–101° C.

EXAMPLE 1c 3-(1H-Tetrazol-1-yl)pyridine; mp 77°–78° C.

We claim:

1. A compound of Formula I

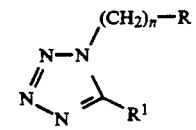

wherein R is selected from the group consisting of

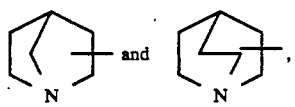

$R^1$ is hydrogen, alkyl of from one to ten carbon atoms, alkynyl of from two to ten carbon atoms or aryl; n is zero or an integer of one or two; or a pharmaceutically acceptable acid addition salt thereof.

2. A compound according to claim 1 selected from the group consisting of:

3-(1H-Tetrazol-1-ylmethyl)-1-azabicyclo[2.2.1]heptane;
3-(1H-Tetrazol-1-ylmethyl)-1-azabicyclo[2.2.2]octane;
3-(1H-Tetrazol-1-yl)-1-azabicyclo[2.2.2]octane;
3-(5-Methyl-1H-Tetrazol-1-yl)-1-azabicyclo[2.2.2]octane; and
3-(5-Ethyl-1H-Tetrazol-1-yl)-1-azabicyclo[2.2.2]octane.

3. A pharmaceutical composition for the treatment of the symptoms of cognitive decline in an elderly patient comprising a cholinergically effective amount of a compound according to claim 1 in combination with a pharmaceutically acceptable carrier.

* * * * *